US009107443B2

(12) United States Patent
Visser et al.

(10) Patent No.: US 9,107,443 B2
(45) Date of Patent: Aug. 18, 2015

(54) LIQUID NISIN COMPOSITIONS

(75) Inventors: Johannes Martinus Jacobus Visser, Delft (NL); Ben Rudolf De Haan, Rijswijk (NL)

(73) Assignee: DSM IP ASSETS B.V., Heerlen (NL)

( * ) Notice: Subject to any disclaimer, the term of this patent is extended or adjusted under 35 U.S.C. 154(b) by 742 days.

(21) Appl. No.: 13/055,981

(22) PCT Filed: Aug. 12, 2009

(86) PCT No.: PCT/EP2009/060413
§ 371 (c)(1),
(2), (4) Date: Jan. 26, 2011

(87) PCT Pub. No.: WO2010/018186
PCT Pub. Date: Feb. 18, 2010

(65) Prior Publication Data
US 2011/0177218 A1 Jul. 21, 2011

(30) Foreign Application Priority Data
Aug. 12, 2008 (EP) .................................. 08162201

(51) Int. Cl.
*A23L 3/34* (2006.01)
*A01N 37/18* (2006.01)
*A23L 3/3463* (2006.01)
*A23B 5/16* (2006.01)
*A23L 2/44* (2006.01)

(52) U.S. Cl.
CPC ............... *A23L 3/34635* (2013.01); *A23B 5/16* (2013.01); *A23L 2/44* (2013.01)

(58) Field of Classification Search
CPC ....... A01N 43/72; A01N 49/00; A01N 63/02; A01N 65/08; A23L 3/34635; A23L 3/3508
USPC ............. 426/321, 654, 532; 514/2.4; 530/317
See application file for complete search history.

(56) References Cited

U.S. PATENT DOCUMENTS 5,217,950 A * 6/1993 Blackburn et al. ............. 514/2.4
2003/0129281 A1 7/2003 Murray

FOREIGN PATENT DOCUMENTS

| AU | 766 707 | | 10/2003 |
| CN | 1820659 A | * | 8/2006 |
| EP | 0 453 860 | | 10/1991 |
| EP | 453860 A1 | * | 10/1991 |
| WO | 92/18143 | | 10/1992 |
| WO | 97/20473 | | 6/1997 |
| WO | 2006/032646 | | 3/2006 |
| WO | WO 2006032646 A1 | * | 3/2006 |

OTHER PUBLICATIONS

Berridge, NJ. Prepration of the antibiotic nisin. Biochemical Journal, vol. 45, 1949, pp. 486-493.*
Rollema, HE; Kuipers, OP; Both, P., de Vos, WM; Siezen, RJ Improvement of Solubility and Stability of the Antimicrobial Peptide Nisin by Protein Engineering. Applied and Environmental Microbiology, 1995, pp. 2873-2878.*
Kelly, NA; Reuben, BG; Rhoades, J and Roller, S. Solvent extraction of bacteriocins from model solutions and fermentation broths. Journal of Chemical Technology and Biotechnology vol. 75, 2000, pp. 777-784.*
International Search Report for PCT/EP2009/060413, mailed Feb. 12, 2010.
International Preliminary Report on Patentability for PCT/EP2009/060413, mailed Nov. 25, 2010.
Berridge, "Preparation of the Antibiotic Nisin", Biochemical Journal, vol. 45, 1949, pp. 486-493, XP002551457.
Cheeseman et al., "An Improved Method of Preparing Nisin", Biochemical Journal, vol. 65, No. 3, 1957, pp. 603-608, XP002551458.
Delves-Broughton "Nisin and its uses as a Food Preservative", Food Technology, Institute of Food Technologists, Chicago, IL, US, vol. 44, No. 11, Nov. 1, 1990, XP000167846.
Nguyen et al., "Potential of a Nisin-Containing Bacterial Cellulose Film to Inhibit *Listeria monocytogenes* on Processed Meats", Food Microbiology, Academic Press, Ltd, London, GB, vol. 25, No. 3, Jan. 29, 2008, pp. 471-478, XP022537813.
Jozala et al., "Liquid-Liquid Extraction of Commercial and Biosynthesized Nisin by Aqueous two-phase Micellar Systems", Enzyme and Microbial Technology, Stoneham, MA, US, vol. 42, No. 2, Dec. 12, 2007, pp. 107-112, XP022387253.
Chinese Office Action dated Aug. 1, 2012; based on Chinese Application No. 200980131530.7 (12 pages).
Yao; "Application of Nisin in food"; China Food Additives; 1996; No. 2; pp. 24-27.
Badr et al.; "Characterization of Nisin Produced by *Lactococcus lactis*"; International Journal of Agriculture & Biology; 2005; vol. 7; No. 3; pp. 499-503 (incorrectly listed on Search Report as pp. 449-503).
Luo et al.; "Chinese Pharmaceutical Necessities"; 2006; the first version; p. 28; Chemical Industry Press.
Holland; "The Purification and Properties of Megacin, a Bacteriocin from *Bacillus megaterium*"; 1961; Biochem. J.; vol. 78; pp. 641-648.
Zhao et al.; "Study on the technology of salt-out for separating Nisin from fermentation broth"; 1996; No. 2; Science and Technology of Food Industry; 2008; vol. 29; No. 2; pp. 226-227; China Academic Journal Electronic Publishing House.

* cited by examiner

*Primary Examiner* — Nikki H Dees
*Assistant Examiner* — Subbalakshmi Prakash
(74) *Attorney, Agent, or Firm* — Miles & Stockbridge PC

(57) ABSTRACT

The present invention relates to liquid nisin compositions having a high anti-microbial activity. The invention further relates to a method for preparing the liquid nisin compositions as well as their use as a preservative in food products.

14 Claims, No Drawings

LIQUID NISIN COMPOSITIONS

This application is the U.S. national phase of International Application No. PCT/EP2009/060413, filed 12 Aug. 2009, which designated the U.S. and claims priority to European Application No. 08162201.1, filed 12 Aug. 2008, the entire contents of each of which are hereby incorporated by reference.

FIELD OF THE INVENTION

The present invention relates to liquid nisin compositions, to methods for preparing the compositions, to their use as a preservative and to methods for preserving food wherein the compositions are used.

BACKGROUND OF THE INVENTION

The need for improved food preservation methods is great. It has been estimated that a large part of the world's food supply is lost as a result of microbial spoilage and food-borne microbial infections represent a constant and serious threat to human health.

Several bacterial species that may contaminate and grow in foodstuffs and crops are pathogenic or produce toxins and cause a range of food-poisoning diseases. Despite substantial improvement in the technology and hygiene, food products may be exposed to spoilage and pathogenic bacteria in the food-handling environment and the number of food poisonings is still increasing in most of the countries. Food preservation techniques, e.g. heat processing, freezing, ultrasound, irradiation, and high pressure treatment, significantly reduce microbial load but of particular concern is the evidence that processed foods are contaminated with micro-organisms following processing and prior to packaging. Of rising concern in the food industry are microbial problems related to various foods such as dairy and meat products, fresh and chilled foods and seafood.

Especially food products in the pH range of 4.5 to 7.0 are known to be susceptible to microbial spoilage by microorganisms, including pathogens and spore forming bacteria. At lower pH levels, yeasts, moulds and acid-tolerant bacteria are most relevant. Mostly, processed foods are not consumed directly after processing, thereby permitting bacteria surviving the production process or introduced by post-contamination to grow. Since food consumption may occur without reheating the processed foods to sufficient temperatures for sufficient time, there is a risk of food poisoning or food spoilage.

Furthermore, the recent trend for minimally processed foods with the intrinsic nutritional and sensory qualities of raw and fresh foods has raised the safety risk. Milder preservation treatments, such as high hydrostatic pressure and pulsed-electric-field techniques have proven to be successful, but often rely on effective hurdles, i.e. cold chain and addition of natural antimicrobials.

There has been extensive research conducted in the field of food safety to develop effective anti-microbial product designs, which result in a combination of compositions, processing and shelf-life conditions.

Nisin is a peptide-like antibacterial substance produced by *Lactococcus lactis* subsp. *lactis*. It comprises 34 amino acids and is active against mainly gram-positive bacteria. Nisin is non-toxic and is free of side-effects. Nisin is a Generally Recognized as Safe substance and is widely used in a variety of foods. Examples of such products are processed cheese, milk, clotted cream, dairy desserts, ice cream mixes, liquid egg, hot-baked flour products, dressings and beer. Nisin is heat-stable and survives pasteurisation temperatures with minimal loss of activity.

Usually, nisin is obtained by fermentation of a species of *Lactococcus lactis* and is further formulated as a dry powder that can be used as a preservative as such or after having first being solved into a suitable solvent. Delvoplus® and Nisaplin® are brand names for a nisin powder containing 1 million IU per gram. They are distributed by DSM and Danisco, respectively. These powdered nisin products have several drawbacks: dust is generated upon handling, and dosing and mixing small amounts of powders into products is difficult. Therefore, liquid nisin compositions which do not have the drawbacks described above are commercially preferred.

Liquid nisin compositions as such are known in the art. Although liquid nisin compositions have been reported to have activity against gram-positive bacteria (see Mota-Meira et al. (2000), Montville et al. (1999), U.S. Pat. No. 5,584,199 and U.S. Pat. No. 4,597,972) and even gram-negative bacteria (see EP 0 453 860, U.S. Pat. No. 5,260,271 and U.S. Pat. No. 5,559,096), there is still a need for liquid nisin compositions having an improved antimicrobial activity, particularly against gram-positive bacteria found in the food industry.

SUMMARY OF THE INVENTION

Surprisingly, nisin compositions having a very high activity against gram-positive bacteria have now been found. Due to their high antimicrobial activity only low amounts of the compositions are needed for effective action against bacteria e.g. gram-positive bacteria. The compositions have good microbiological stability which in combination with their good physical and chemical stability makes the compositions suitable for prolonged storage and ergo gives them a long shelf life. In addition, the compositions of the invention can have a low turbidity, which makes them suitable for use in food applications, wherein addition of low turbidity additives is of importance. In the light of the above characteristics, the compositions of the invention can advantageously be employed as food preservatives.

DETAILED DESCRIPTION OF THE INVENTION

According to a first aspect the invention provides a method for preparing a liquid nisin composition, preferably an aqueous liquid nisin composition. The method comprises the steps of: a) preparing a first liquid nisin containing composition having a pH of about 1.5 to about 12, preferably about 3 to about 10, preferably about 3.5 to about 9.5, more preferably about 4 to about 9, yet more preferably about 4.5 to about 8.5, even more preferably about 5 to about 8, most preferably about 5.5 to about 7.5, and in particular about 5.5 to below 7, b) isolating solid compounds from the prepared first liquid nisin containing composition, c) contacting the isolated solid compounds with a solution having a pH of about 0 to about 5, preferably about 0.5 to about 4.5, more preferably about 1 to about 4, even more preferably about 1.5 to about 3.5, most preferably about 1.5 to about 3 and in particular about 2 to about 3 to prepare a second liquid nisin composition, and d) removing solid compounds from the second liquid nisin composition. Step d is optional, but in a preferred embodiment it is performed in the method of the invention.

In a further embodiment the method of the invention comprises the step of: e) adjusting the pH of the second liquid nisin composition to a desired pH-value such as a pH between 2 and 6, e.g. a pH between 2 and 3 or a pH between 5 and 6.

Optionally, at least one of the additional functional compounds mentioned below can be added before, during or after at least one of the steps of the method of the invention. For instance, a cryoprotectant, e.g. glycerol, can be added during step c, such that the second liquid nisin composition comprises 35% to 60% w/w cryoprotectant. In another example, a compound that decreases or diminishes foam formation and/or an additional antimicrobial compound, e.g. an organic acid or a salt thereof, can be added before step b. In a preferred embodiment however at least one additional functional compound is added after step d and prior to step e, or during or after step e.

In an embodiment step a comprises mixing nisin with an aqueous solution to prepare a first liquid nisin containing composition having a final inorganic salt (e.g. NaCl) concentration of 1.5 M or below, preferably 0.05 M to 1.5 M and more preferably 0.1 M to 1.5 M. The first liquid nisin containing composition has a pH of about 1.5 to about 12, preferably about 3 to about 10, preferably about 3.5 to about 9.5, more preferably about 4 to about 9, even more preferably about 4.5 to about 8.5, yet even more preferably about 5 to about 8 and most preferably about 5.5 to about 7.5 and in particular about 5.5 to below 7. Any source of nisin can be suspended and/or dissolved in the aqueous solution. In a preferred embodiment the nisin is a powder, preferably a dry powder. For example, commercially available nisin powder compositions such as Delvoplus® and Nisaplin® can be used. The source may comprise nisin A, nisin Z or a combination thereof. The aqueous solution may be a buffer solution, e.g. a phosphate buffer such as $NaH_2PO_4/Na_2HPO_4$. Other suitable buffers can of course also be used. These include, but are not limited to, acetate buffers, lactate buffers, citrate buffers, glycine/HCl buffers and any combination thereof.

Solid compounds can be separated/isolated from the first liquid nisin containing composition by well-known isolation techniques. In a preferred embodiment step b is performed by means of centrifugation, filtration or any combination thereof.

Subsequently, a second liquid nisin composition can de prepared by e.g. contacting, e.g. dissolving or mixing or suspending, the isolated solid compounds with/in a solution, preferably an aqueous solution, having a pH of about 0 to about 5, preferably about 0.5 to about 4.5, more preferably about 1 to about 4, even more preferably about 1.5 to about 3.5, most preferably about 1.5 to about 3 and in particular about 2 to about 3. In an embodiment an additional functional compound mentioned below is added during this step.

Next, the second liquid nisin composition can be purified by removing e.g. the remaining debris and/or non-nisin proteins or parts thereof. This purification step can be performed by well-known isolation techniques. In a preferred embodiment step d is performed by means of centrifugation, filtration or any combination thereof.

The above-described method results in a liquid nisin composition having a much higher activity against micro-organisms, particularly gram-positive bacteria, than liquid nisin compositions described in the prior art. In other words, the method of the present invention results in liquid nisin compositions having a much lower minimum inhibitory concentration (MIC) against micro-organisms, particularly gram-positive bacteria, than liquid nisin compositions described in the prior art.

Therefore, a nisin composition obtainable by a method according to the invention is another part of the present invention. The nisin composition may be solid, but preferably it is a liquid composition.

In an embodiment the nisin compositions of the invention have a MIC of 1.0 µg/ml or less against at least one gram-positive bacterium. MIC refers to the minimum concentration of a compound or composition necessary to inhibit growth of the organism tested. Preferably, the MIC is an average of at least three independent repetitions. Compositions of the present invention having a MIC of 1.0 µg/ml or less when tested for growth inhibition of at least one gram-positive bacterium in the assay described herein. In an embodiment the compositions of the invention have a MIC of 0.5 µg/ml or less, preferably a MIC of 0.1 µg/ml or less, more preferably a MIC of 0.05 µg/ml or less, even more preferably a MIC of 0.01 µg/ml or less, yet even more preferably a MIC of 0.005 µg/ml or less, particularly a MIC of 0.001 µg/ml or less, more particularly a MIC of 0.0005 µg/ml or less against at least one gram-positive bacterium and most particularly a MIC of 0.0001 µg/ml or less against at least one gram-positive bacterium. Gram-positive bacteria include, but are not limited to, *Micrococcus* sp., *Listeria* sp., *Bacillus* sp., *Staphylococcus* sp., *Clostridium* sp., *Streptococcus* sp., *Lactobacillus* sp. and *Lactococcus* sp. In an embodiment the gram-positive bacterium is selected from the group consisting of *Bacillus*, *Lactococcus*, *Staphylococcus*, *Listeria* and *Micrococcus*. Suitable species within the genera *Bacillus*, *Lactococcus*, *Staphylococcus*, *Listeria* and *Micrococcus* include, but are not limited to, *B. subtilis*, *L. lactis*, *S. aureus*, *L. innocua* and *M. luteus*, respectively. Within the species given suitable strains include, but are not limited to, *Bacillus subtilis* ATCC 31578, *Lactococcus lactis* ATCC 19257, *Staphylocoocus aureus* ATCC 27661, *Listeria innocua* LMD 92.20 and *Micrococcus luteus* B212, respectively. In a preferred embodiment the compositions of the present invention have a MIC of 0.5 µg/ml or less, preferably a MIC of 0.1 µg/ml or less, more preferably a MIC of 0.05 µg/ml or less, even more preferably a MIC of 0.01 µg/ml or less, yet even more preferably a MIC of 0.005 µg/ml or less, particularly a MIC of 0.001 µg/ml or less and more particularly a MIC of 0.0005 µg/ml or less against at least one strain of *M. luteus*, preferably *M. luteus* B212.

Nisin activity can be measured using the following bioassay well-known to the skilled person (see Pongtharangkul and Demirci, 2004), including pre-treating the nisin composition at low pH. Briefly, *M. luteus* B212 containing agar plates (Iso-sensitest agar) are prepared using a freshly grown culture. After drying, a vacuum pump is used to create small holes in the agar. Samples and dilutions thereof (10 µl) are transferred into the holes and allowed to diffuse into the agar for 18 hours at 5° C. Subsequently, the agar plates are incubated for 24 hours at 30° C. and the inhibition zones around the sample containing holes are measured. Parallel to the samples, controls with known amounts of nisin (0-1600 IU/ml) are included. Their inhibition zones are used to prepare a calibration curve required to determine the nisin levels of the samples. All steps are carried out aseptically. The IU for nisin has already been defined as follows. The World Health Organization Committee on Biological Standardization, Twenty second report. World Health Organization Technical Report Series, No. 444 in 1970, has established an international reference preparation of nisin, and the international unit (IU hereinafter) is defined as 0.001 mg of this preparation. Delvoplus® and Nisaplin®, brand names for nisin powder products containing 1 million IU per gram, are distributed by DSM and Danisco, respectively. By means of the above assay the nisin concentration in samples can be determined.

The MIC of nisin compositions can be measured by means of the following MIC assay. Nisin activity is measured using the standard microdilution broth assay, well-known to the skilled person. Briefly, a *Micrococcus luteus* B212 containing Iso-sensitest broth is prepared using a freshly grown culture. The number of cells per ml is determined using a counting chamber. Preferably, a cell count of $10^3$ is used. 100 µl of inoculum is added to each well of a 96-well microtiter plate. 100 µl of a nisin composition is added to the first well (A1) and mixed properly by pipetting up and down three times. A serial dilution is made by transferring 100 µl of the first well to the next well (A2) and diluted properly. This is repeated until each component is serially diluted in 36 wells. Next, plates are incubated at 30° C. for 7 days and read each day for bacterial growth. MIC concentrations are the lowest concentration completely inhibiting growth.

In an embodiment the compositions of the invention have a pH of about 0 to about 5, preferably about 0.5 to about 4.5, more preferably about 1 to about 4, even more preferably about 1.5 to about 3.5, most preferably about 1.5 to about 3 and in particular about 2 to about 3. At such pH conditions, the microbiological stability of the compositions of the invention is good and the MIC of the compositions is low and stable during storage.

In a further embodiment the compositions according to the invention comprise 0.01 to 5%, preferably 0.05 to 2.5%, more preferably 0.1 to 1.0%, most preferably 0.15 to 0.5% and in particular 0.2 to 0.3% (w/w) nisin.

The nisin compositions of the invention may comprise a low amount of salts such as inorganic salts e.g. NaCl. It is to be understood that the additional functional compounds mentioned below (e.g. antimicrobial compounds such as organic acids or their salts) are not meant to be included within the definition of "salt". In an embodiment the compositions of the invention comprise a salt, e.g. inorganic salt, to nisin ratio of 100:1 to 1:100, preferably 50:1 to 1:100, more preferably 25:1 to 1:100 and in particular 10:1 to 1:100. In an embodiment the nisin compositions of the invention are essentially free of salts, preferably inorganic salts such as e.g. NaCl. The inorganic salt may be any suitable, food grade inorganic salt. Examples of inorganic salts are NaCl, $Na_2SO_4$, $(Ca)_3(PO_4)_2$, $KNO_3$, KCl and $MgCO_3$. The concentration of these salts in the compositions is 100 mg/ml or less, preferably 50 mg/ml or less, more preferably 25 mg/ml or less and in particular 15 mg/ml or less. The salt concentration may be measured by separate cationic analysis, by atomic absorption anionic analysis, by HPLC or preferably by determination of the ash content by ignition (550+/−25° C.). Nisin compositions having a low concentration of inorganic salts are very attractive, since they will not interfere with the food matrix to give undesired reactions and alterations of taste and/or structure.

The nisin compositions of the invention may comprise low amounts of components other than nisin and salt. These components may be proteins or parts thereof. It is to be understood that the additional functional compounds mentioned below (e.g. antimicrobial compounds, anti-foaming agents, surfactants, etc.) are not meant to be included within the definition of "components other than nisin and salt". In an embodiment the compositions of the invention comprise a non-nisin component to nisin ratio of 100:1 to 1:100, preferably 10:1 to 1:100 and more preferably 2:1 to 1:100. In an embodiment the nisin compositions of the invention are essentially free of these components. The components may originate from the biomass produced during the nisin fermentation process using *Lactococcus lactis*. The nisin concentration may first be measured by the assay described above. Subsequently, total protein concentration may be estimated using classical assays known to the skilled person. The non-nisin protein concentration may be estimated by subtracting the nisin concentration from the total protein concentration.

In yet another embodiment the compositions of the invention are clear liquid compositions. Clear liquid nisin compositions can be used on and/or in any type of product. In view of their clarity, they can advantageously be used in products wherein clarity is of importance such as jelly-based products e.g. jelly dessert, fruit juices, beverages and surface applications on food products. Clear liquid compositions as used herein are liquid compositions having a turbidity of 0 to 100 FNU, preferably 0 to 50 FNU, more preferably 0 to 25 FNU and particularly 0 to 10 FNU. Turbid liquid compositions are liquid compositions having a turbidity of above 100 FNU. The turbidity in FNU (Formazine Nephelometric Unit) can be determined with a light scattering method and can be measured using a Nephla turbidity photometer with measuring method DIN EN 27027/ISO 7027. Clear as well as turbid liquid nisin compositions can be prepared by means of the method according to the invention. A clear liquid composition is prepared, if a liquid nisin containing composition having a pH of about 5 or higher, preferably a pH of about 5 to about 9, is prepared in step a of the method of the invention. A turbid liquid composition is prepared, if a liquid nisin containing composition having a pH of below about 5, preferably a pH of about 1.5 to below about 5, or a pH of above about 9, preferably a pH of above about 9 to about 12 is prepared in step a of the method of the invention. Both the clear and the turbid liquid nisin compositions have the above-described high activity against micro-organisms, in particular gram-positive bacteria.

A method wherein the final inorganic salt (e.g. NaCl) concentration of the first liquid nisin containing composition (i.e. the liquid nisin composition prepared in step a of the method according to the invention, see above) is above 1.5 M has several disadvantages compared to a method wherein the final inorganic salt concentration of the first liquid nisin containing composition is 1.5 M or below. Firstly, the first liquid nisin composition having a final inorganic salt concentration of above 1.5 M shows a decreased separation performance in centrifugation (i.e. has lower sedimentation rate) in comparison to liquid nisin compositions with a final inorganic salt concentration of 1.5 M or below. Secondly, the resulting final liquid nisin composition that is prepared by performing the method according to the present invention (i.e. steps a to c and optionally steps d and e, see above) wherein the first liquid nisin containing composition has a final inorganic salt concentration of above 1.5 M has several disadvantages:

it is turbid;

It has a lower purity than final liquid nisin compositions that have been made by means of a method according to the present invention wherein the first liquid nisin containing composition contains a final inorganic salt concentration of 1.5 M or below;

It has a lower antimicrobial activity than final liquid nisin compositions that have been made by means of a method according to the present invention wherein the first liquid nisin containing composition contains a final inorganic salt concentration of 1.5 M or below; and It has a higher risk to precipitate than final liquid nisin compositions that have been made by means of a method according to the present invention wherein the first liquid nisin containing composition contains a final inorganic salt concentration of 1.5 M or below The liquid nisin compositions of the invention have at least one of the advantages listed below compared to liquid nisin preparations known in the prior art:

the compositions of the invention have a better antimicrobial efficacy compared to liquid nisin compositions of the prior art, and/or the compositions of the invention are essentially free of salts such as e.g. inorganic salts e.g. NaCl and essentially free of other non-nisin components. As a result thereof, in food applications, the use of the compositions of the invention do not interfere with the food matrix to give undesired reactions and alterations of the taste and/or structure are avoided, and/or the compositions of the invention can be clear, i.e. have a low turbidity (between 0 and 100 FNU). Such compositions do not interfere with the colour and/or clarity of the products to which they are applied.

According to another embodiment, the compositions of the invention further comprise at least one additional functional compound including, but not limited to, an additional antimicrobial compound such as an acid e.g. sorbic acid, propionic acid, benzoic acid, acetic acid, lactic acid, citric acid, cinnamic acid, or a salt of any of these acids, a glucose oxidase, natamycin, lysozyme, poly-L-lysine, nystatin, lucensomycin, amphotericin B, filipin, pediocin; a surfactant e.g. SDS, Tween, fatty acids; a pH adjusting agent such as HCl or NaOH or a buffering agent e.g. a phosphate salt or acetate salt; a cryoprotectant such as glycerol or propanediol; a thickening agent e.g. xanthan gum, guar gum, Arabic gum, tragacanth gum, gellan gum, locust bean gum, carrageenan gum, rhamxan gum, alginate, starch, carboxymethyl cellulose, carboxyethyl cellulose, hydroxypropylmethyl cellulose, hydroxypropyl cellulose, methyl cellulose, polyvinyl alcohol, polyethylene glycol, polypropylene glycol. Moreover, the compositions of the invention may comprise agents that decrease or diminish foam formation. The additional compounds may be added to the compositions of the invention in solid or liquid form and may be mixed well in advance or directly prior to use. Using at least one additional antimicrobial compound/preservative in the nisin compositions of the invention is expected to further stabilize it microbiologically and therefore may be beneficial for its shelf-life.

The activity of nisin present in an aqueous liquid composition can be substantially increased by removing impurities. Moreover, the solubilisation rate of nisin in aqueous compositions is increased by the removal of impurities such as e.g. inorganic salts. Nisin may be partly bound to the impurities resulting in nisin which is non-available for its preservative activity. In other words, nisin has a limited bioavailability in the presence of impurities. As used herein, the term "bioavailability" refers to the availability, amount (e.g., concentration), or activity of nisin in a liquid, semi-solid or solid formulation. Impurities such as non-nisin proteins or other non-nisin components, cell wall debris and salts may have a negative effect on the solubilisation rate of nisin. Approximately, less than 50% of the nisin present in such liquid formulation is found to be available as a preservative in case these impurities are present. The impurities have been found to be present in commercially available nisin products. Commercially available nisin contains in general 5-25% on non-nisin protein and cell debris. These impurities originate from the production process of the nisin. In the recovery, purification or reformulation following the fermentation salts are often used which still are present in the final nisin formulation.

In a further aspect the invention relates to an aqueous suspension of nisin comprising a thickening agent. Of course, two or more different thickening agents can also be used. The suspensions of the invention comprise 0.01 to 5%, preferably 0.05 to 2.5%, more preferably 0.1 to 1%, most preferably 0.15 to 0.5% and in particular 0.2 to 0.3% (w/w) nisin. The suspensions of the invention comprise 0.01 to 5%, preferably 0.05 to 5%, more preferably 0.1 to 5%, most preferably 0.2 to 5% and in particular 0.5 to 5% (w/w) thickening agent. The thickening agent is selected from the group consisting of xanthan gum, guar gum, Arabic gum, tragacanth gum, gellan gum, locust bean gum, carrageenan gum, rhamxan gum, alginate, starch, carboxymethyl cellulose, carboxyethyl cellulose, hydroxypropylmethyl cellulose, hydroxypropyl cellulose, methyl cellulose, polyvinyl alcohol, polyethylene glycol and polypropylene glycol. In a preferred embodiment the thickening agent is a gum such as xanthan gum. The pH of the suspension according to the invention is about 2 to about 12, preferably about 2 to about 11, more preferably about 2 to about 10, even more preferably about 2 to about 9, yet even more preferably about 2 to about 8, most preferably about 2 to about 7 and in particular about 2 to about 6. The suspension of the invention is stable. "Stable suspension" as used herein means a physically stable suspension, i.e. a suspension that shows 50% or less, preferably 40% or less, more preferably 30% or less, even more preferably 20% or less, most preferably 10% or less and in particular 0% sedimentation after storage at room temperature for 9 days at pH 5. The physical stability of the suspensions can be measured by methods known in the art such as the sedimentation assay as shown herein (see Example 9).

In an embodiment the suspension according to the invention further comprises at least one additional functional compound selected from the group consisting of an additional antimicrobial compound, a surfactant, a pH adjusting agent, and a cryoprotectant. Examples of suitable additional antimicrobial compounds are acids such as sorbic acid, propionic acid, benzoic acid, acetic acid, lactic acid, citric acid, cinnamic acid, or salts of any of these acids, a glucose oxidase, natamycin, lysozyme, poly-L-lysine, nystatin, lucensomycin, amphotericin B, filipin, pediocin. Examples of suitable surfactants are SDS, Tween, fatty acids, to name just a few. Examples of suitable pH adjusting agents are among others HCl or NaOH or buffering agents such as phosphate salts and acetate salts. Examples of suitable cryoprotectants are glycerol and propanediol. Moreover, the suspensions of the invention may comprise agents that decrease or diminish foam formation. The additional compounds may be added to the suspensions of the invention in solid or liquid form and may be mixed well in advance or directly prior to use.

In a further embodiment the invention relates to a method of preparing a suspension according to the invention, the method comprising the steps of: a) adding nisin and a thickening agent, either separately or as a powder composition, to an aqueous solution (e.g. water), and b) mixing to obtain a suspension. If necessary, the pH of the suspension can be adjusted to a pH of about 2 to about 12, preferably about 2 to about 11, more preferably about 2 to about 10, even more preferably about 2 to about 9, yet even more preferably about 2 to about 8, most preferably about 2 to about 7 and in particular about 2 to about 6.

The nisin and thickening agent can be added separately to the aqueous solution. They can be in powder form or in liquid form. Alternatively, nisin and the thickening agent can be present in one powder composition and this powder composition can be added to the aqueous solution. So, in a further embodiment the invention relates to a powder composition comprising nisin and a thickening agent. Nisin and/or the thickening agent can be added together with an additional functional compound described above to the aqueous solution and then mixed to obtain a suspension. Alternatively, the additional functional compounds can be added after the suspension comprising nisin and thickening agent has been obtained. In a further embodiment nisin is first added to the aqueous solution, followed by an additional functional compound and thereafter the thickening agent is added and the solution is mixed to obtain a suspension. In yet a further embodiment a thickening agent is first added to the aqueous solution, followed by an additional functional compound and thereafter nisin is added and the solution is mixed to obtain a suspension. In again a further embodiment the additional functional compound is first added to the aqueous solution, followed by addition of a thickening agent and/or nisin.

Another aspect of the invention is concerned with the use of an aqueous suspension according to the invention for preparation of a treatment liquid for treatment of a food, feed or agricultural product. The treatment liquid can be prepared by mixing an aqueous solution with the suspension according to the invention. Treatment of the food, feed or agricultural product can be done by spraying, dipping, immersion, brushing to name just a few.

According to a further aspect, the invention provides the use of a composition or suspension according to the invention as a preservative in and/or on food, feed or agricultural products. Hereafter, the term "suspension" also includes a treatment liquid prepared from a suspension according to the invention. The compositions and suspensions of the invention do not have drawbacks associated with powder formulations: they are more easy-to-use (ease of dosing) and there is no dust formation when using them. Additionally, foam formation and dissolving problems that occur when solubilising nisin powder into a solvent are prevented. Effective levels of nisin to preserve food products range from 1 to 1500 IU/g or 0.025 to 37.5 ppm of nisin. The compositions and suspensions according to the invention can be used alone, but also in combination with other antimicrobial compositions, e.g. compositions comprising organic acids or salts thereof, lysozyme. The antimicrobial compositions can be applied to food, feed or agricultural products before, during or after application of the compositions or suspensions according to the invention.

In a further aspect the invention pertains to a container comprising 1 to 1000 liter of a composition or suspension according to the invention. The container can be a bottle, bag or tank, to name just a few.

According to a further aspect, the invention provides a method for preserving food, feed or agricultural products, wherein the nisin compositions or suspensions of the invention are being used, e.g. applied in and/or on the respective products. The nisin compositions and suspensions can be applied by spraying, dipping, immersion, brushing, to name just a few methods. In case the substrate/product is a liquid or semi-liquid, they may be directly added. The compositions or suspensions may even leave a coating, e.g. an antimicrobial coating, on the substrate they are applied to/on. Optionally, in a further step, the product may also be pasteurised/sterilized. This step may of course also be performed before application of the nisin compositions or suspensions of the invention. All types of food products may be treated with the compositions or suspensions of the invention. The food products may be dairy food products; food products containing or derived from eggs, meats, especially poultry e.g. freshly slaughtered poultry, vegetables, crustacean and fish; rice products such as boiled rice products; bakery food products; beverages; chilled food products; clear food products such as jelly-based food products such as jelly desserts; juices; spreads; jam; canned fruit and other canned products; food products wherein the compositions or suspensions of the invention are applied to on the surface. Dairy food products include, but are not limited to, processed cheese, milk, clotted cream, dairy desserts, ice cream mixes, dressing and yoghurts. The compositions and suspensions according to the invention can also be used in the treatment of food packaging and handling equipment and can be included in/on packaging materials used for packaging of food, feed or agricultural products. The compositions and suspensions of the invention may also be used as a disinfectant for cleaning surfaces and cooking utensils in food processing plants and any area in which food is prepared or served such as hospitals, nursing homes, restaurants, especially fast food restaurants, delicatessens and the like. The compositions and suspensions according to the invention are capable of inhibiting bacterial growth in products for an extended period of time, for example at least about 1 day, 2, 3, 4, 5, 10, 15, 20, 25, 30, 35, 40, 45, 50, 55, 60, 65, 70, 75, 80, 85, 90, 95, 100, 150, 200, 250, 300, 400, 500, 600, 700, 800, 900 days and preferably at least about 1000 days. The compositions and suspensions according to the invention can be used to prevent bacterial growth, e.g. the growth of Gram-positive bacteria such as *Staphylococcus, Streptococcus, Listeria*, and *Coryneform* bacteria. It can even be used to prevent growth of Gram-negative bacteria such as Gram negative bacteria such as *Salmonella, Shigella, Escherichia Coli, Klebsiella, Pseudomonas, Bacterioides*, and *Actinobacillus* bacteria.

Ergo, a food, feed, or agricultural product comprising a nisin composition or suspension according to the invention is another part of the invention.

In yet another aspect, the invention pertains to a method for producing a solid, e.g. powder, nisin composition comprising the step of subjecting the liquid nisin composition according to the invention to e.g. a drying step, lyophilisation step, crystallisation step (followed if necessary by filtration or centrifugation) or a precipitation step (followed if necessary by filtration or centrifugation), to name just a few. The steps may be performed immediately after step c, d or e of the method for preparing the nisin compositions of the invention as described above. They may also be done after the liquid nisin compositions of the invention have been stored for a period of time. The resulting solid/powder nisin compositions can be mixed with powder compositions comprising other suitable compounds such as e.g. the additional functional compounds described above.

The invention is further illustrated by the following examples, which should not be construed as limiting the scope of the invention.

EXAMPLES

Example 1

Preparation of Liquid Nisin Compositions

The following liquid nisin compositions were prepared:
Composition A: Ten grams of nisin powder Nisaplin® (Danisco, Denmark) containing 2.5% w/w nisin and at least 50% w/w NaCl was dissolved in an aqueous HCl solution (pH 2.0-3.0; total volume 100 ml).
Composition B: Ten grams of nisin powder Nisaplin® (Danisco, Denmark) containing 2.5% w/w nisin and at least 50% w/w NaCl was dissolved in an aqueous HCl solution (pH 5.5-6.5; total volume 100 ml).
Compositions C and D: Ten grams of nisin powder Nisaplin® (Danisco, Denmark) containing 2.5% w/w nisin and at least 50% w/w NaCl was dissolved in a buffered aqueous solution of 0.2 M sodiumdihydrogenphosphate and disodiumhydrogenphosphate (pH 7.0; total volume 100 ml; in addition composition having a pH of 6 and compositions having a pH of 6.5 were made). The mixture was subsequently mixed for about 15 minutes. The mixture was centrifuged at 4,500×g for 15 minutes at 10° C. and a pellet containing nisin was obtained. Subsequently, the pellet was dissolved in an aqueous citric acid solution (pH 2.0 to 3.0; total volume 100 ml). The mixture was stirred for 15 minutes. The obtained solution containing nisin was centrifuged at 4,500×g for 15 minutes at 10° C. to remove remaining solid components. The obtained liquid compositions were either kept at a pH of 2.0 to 3.0 (Composition C) or the pH was adjusted to a pH between 5.5 and 6.5 by addition of NaOH (Composition D).

Compositions E and F: The preparation of compositions E and F was identical to the preparation of compositions C and D with the proviso that the pellet was dissolved in an aqueous HCl solution having a pH of 2.0 to 3.0.

Compositions G and H: Ten grams of nisin powder Nisaplin® (Danisco, Denmark) containing 2.5% w/w nisin and at least 50% w/w NaCl was dissolved in an aqueous HCl solution (pH 2.0-3.0; total volume 100 ml). The obtained mixture was dialysed for 24 hours in an aqueous HCl solution of pH 2.0 to 3.0. Next, the dialysed mixture was centrifuged at 4,500×g for 15 minutes at 10° C. The obtained liquid compositions were either kept at a pH of 2.0 to 3.0 (Composition G) or the pH was adjusted to a pH between 5.5 and 6.5 by addition of NaOH (Composition H). The obtained compositions were used in the following experiments.

Example 2

MIC Assay

For the MIC assay freshly cultured *Micrococcus luteus* cells (B212) and *Pseudomonas aeruginosa* cells (ATCC 9027) were obtained from an overnight culture grown in Iso Sensitest Broth (Oxoid) and Plate Count Broth (Difco), respectively, at 30° C. A stock suspension of $4.3 \times 10^5$ and $2.5 \times 10^4$ colony forming units CFU/ml, respectively, was prepared in physiological saline. 30 µl of the respective stock solution was added to 30 ml of Iso Sensitest Broth (suspension A) and Plate Count Broth (suspension B), respectively. Then, 100 µl of suspension A was transferred to each well of a first 96-wells microtiter plate and 100 µl of suspension B was transferred to each well of a second 96-wells microtiter plate. Nisin compositions were prepared according to Example 1. 100 µl of a nisin composition was used in a standard micro dilution broth assay to determine the Minimal Inhibition Concentration (MIC) of each nisin composition. The results, presented in Table 1, show that the nisin compositions C, D, E and F show the highest activity (i.e. lowest MIC) against both micro-organisms (a gram-positive micro-organism, i.e. *M. luteus*, and a gram-negative micro-organism, i.e. *P. aeruginosa*) at pH 2.5 and pH 6.0. The MIC of compositions C and E is between about 40- to about 100-fold lower than the MIC of compositions A and G (compositions all having a pH of 2.5), while the MIC of compositions D and F is significantly lower than the MIC of compositions B and H (compositions all having a pH of 6.0). The MIC of compositions C and D prepared with 0.1 M phosphate buffer at pH 7 was comparable to the MIC of compositions C and D prepared with 0.2 M phosphate buffer at pH 6 or pH 6.5.

In a separate experiment the MIC concentrations of compositions A and C were compared for freshly cultured *Bacillus subtilis* (ATCC 31578), *Staphylococcus aureus* (ATCC 27661), *Lactococcus lactis* (ATCC 19257) and *Listeria innocua* (LMD92.20). The experiment was done identically to the experiment described above, with the proviso that the stock suspension prepared contained $1.0 \times 10^6$, $1.3 \times 10^6$, $7.7 \times 10^4$, and $2.8 \times 10^5$ CFU/ml of the respective micro-organism, respectively. The results show that the MIC of composition C for the gram-positive micro-organisms tested is between about 5- to about 300-fold lower than the MIC of composition A (data not shown). The MIC of composition C prepared with 0.1 M phosphate buffer at pH 7 was comparable to the MIC of composition C prepared with 0.2 M phosphate buffer at pH 6 or pH 6.5.

Example 3

Use of Liquid Nisin Compositions in a Baking Application

Two cakes were prepared. For each cake 1000 grams of Moscovisch Powder Damco was mixed with 800 grams of liquid eggs and 100 grams of water. One cake was prepared by adding 120 mg nisin powder Nisaplin® (Danisco, Denmark) to the liquid eggs. A second cake was prepared by adding the 1.2 gram of composition C to the liquid eggs. The same amounts of nisin were used in both cakes (150 mg nisin/l egg). The mixture was mixed during 10 minutes in a Hobart mixer in the third gear, and baked in a 170° C. oven for 25 minutes. Both cakes were baked the same way.

The baked cake comprising composition C showed a fine, woolly crumb structure, while the cake comprising nisin powder showed a hard irregular crumb structure. This clearly shows that baked products wherein the compositions of the invention are used have a better structure than baked products wherein nisin powder is used. The structure of a bakery product is improved by adding a nisin composition according to the invention when compared to adding nisin powder. The example also shows that the compositions according to the invention can be added to the product before baking.

Example 4

Use of Liquid Nisin Compositions in a Beverage Application

In this experiment composition A and C were tested for their ability to decrease the viable count of different contaminating micro-organisms in a beverage application. Compositions A and C were prepared according to Example 1, using nisin powder from Silver Elephant, China. The beverage used was a malt drink, Pony from Bavaria, Colombia. For the experiment freshly cultured *Listeria monocytogenes* cells (LMD 92.20), *Leuconostoc oenos* cells (ML-34) and *Leuconostoc mesenteroides* cells isolated from a contaminated product were obtained from an overnight culture grown at 30° C. in Plate Count Broth (Difco). Stock suspensions of $3.8 \times 10^5$, $5.7 \times 10^6$ and $7.2 \times 10^5$ CFU/ml, respectively, were prepared in physiological saline. 25 µl of the respective stock solutions was added to 25 ml of beverage spiked with composition A or C. The nisin concentration tested was 0.5 ppm for *Listeria monocytogenes* cells, 4 ppm for *Leuconostoc oenos* cells and 2 ppm for *Leuconostoc mesenteroides* cells. A control comprising no nisin was included for each micro-organism. The samples were incubated at room temperature and the total count of micro-organisms (in CFU/ml) was measured at different time intervals using well known methods.

The results are shown in Table 2. They clearly demonstrate that for each of the three different micro-organisms tested composition C reduces the viable cell count to below the detection limit of 1 CFU/ml in less than one day, while composition A needs two or three days to accomplish this. So, composition C is at least 24-48 hours faster than composition A.

Example 5

Use of Liquid Nisin Compositions in a Food Application Model

In this experiment compositions A and C were tested for their ability to decrease the viable count of *Listeria monocytogenes* in a food application model. After decrease of the viable cell count to below the detection limit of 10 CFU/ml the nisin compositions were also tested for their ability to maintain this low level and prevent outgrowth of surviving cells. Compositions A and C were prepared according to Example 1, using nisin from Silver Elephant, China. The application model was prepared using Plate Count Broth (Difco). The pH of the medium was set at pH 7.0 with HCl and autoclaved for 15 minutes at 121° C. For the experiment freshly cultured *Listeria monocytogenes* cells (LMD 92.20) were obtained from an overnight culture grown in Plate Count Broth (Difco) at 30° C. A stock suspension of $3.4\times10^7$ CFU/ml was prepared in physiological saline. 250 µl of the stock solution was added to 25 ml of model medium spiked with composition A or C. The nisin concentration tested was 2.5 µg/ml for the experiment at 10° C. and 6.25 and 12.5 µg/ml for the experiment at room temperature. A control comprising no nisin was included for each temperature tested. The samples were incubated at 10° C. and at room temperature and the total count of micro-organisms (in CFU/ml) was measured at different time intervals using well known methods.

The results clearly demonstrate that composition C inhibits the outgrowth of *Listeria monocytogenes* in a food application model at 10° C. for more than 25 days, while composition A only inhibits the outgrowth for four days (see Table 3). The results further show that composition C inhibits the outgrowth of *Listeria monocytogenes* in a food application model at room temperature for more than 25 days, while composition A only inhibits the outgrowth for two or three days (see Table 4).

Example 6

Preparation of Liquid Nisin Compositions on Pilot Scale Using Centrifugation 100 kg of nisin powder (Silver Elephant, China) containing 2.5% w/w nisin and at least 50% w/w NaCl was dissolved in water. The pH was set to 7.0 with NaOH. The mixture was subsequently mixed for about one hour. An anti-foaming agent (Clerol FBA 3107) was added at 1.5 g/kg mixture. The mixture was subjected continuous centrifugation at 10° C. at 12,000×g with a feed rate of 200 l/h. The concentrate containing nisin solids was recovered. Subsequently, the concentrate was dissolved in an aqueous HCl solution (pH 2.0 to 3.0; mass of complete mix: 1000 kg). The mixture was stirred for at least one hour. The obtained solution containing nisin was again subjected to continuous centrifugation at 10° C. at 12,000×g with a feed rate of 200 l/h followed by depth filtration (with a filter having a pore size of 3 micron) and sterile filtration to remove remaining solid components. The obtained liquid composition was kept at a pH of 2.0 to 3.0. The turbidity of the final product was 21 FNU, i.e. a clear liquid composition was obtained. The obtained liquid nisin composition had a good antimicrobial activity, i.e. a MIC comparable to the MIC of composition C (see Example 2).

The above process was also performed without performing the second continuous centrifugation step. The final product had the same properties as the final product described above.

In addition, the process was performed without the second continuous centrifugation step and without the depth filtration step. The resulting product also had the same properties as the final product described above.

Example 7

Preparation of Liquid Nisin Compositions on Pilot Scale Using Filtration 100 kg of nisin powder (Silver Elephant, China) containing 2.5% w/w nisin and at least 50% w/w NaCl was dissolved in a buffered aqueous solution of 0.2 M sodiumdihydrogenphosphate and disodiumhydrogenphosphate (pH 7.0; mass of complete mix: 1000 kg). The mixture was subsequently mixed for about one hour. The mixture was filtered by dead-end filtration at 10° C. using Dicalite BF filter aid. The filter cake containing nisin solids was recovered. Subsequently, the filter cake was dissolved in an aqueous citric acid solution (pH 2.0 to 3.0; mass of complete mix: 1000 kg). The mixture was stirred for at least one hour. The obtained solution containing nisin was subjected to dead-end filtration, depth filtration and sterile filtration at 10° C. to remove remaining solid components. The obtained liquid composition was kept at a pH of 2.0 to 3.0. The turbidity of the final product was 25 FNU, i.e. a clear liquid composition was obtained. The obtained liquid nisin composition had a good antimicrobial activity, i.e. a MIC comparable to the MIC of composition C (see Example 2).

Example 8

Preparation of Liquid Nisin Compositions Using Filtration at Low pH 100 g of nisin powder (Silver Elephant, China) containing 2.5% w/w nisin and at least 50% w/w NaCl was dissolved in water. The pH was set to 4.0 with NaOH. The mixture was subsequently mixed for about one hour. The mixture was filtered by dead-end filtration at 10° C. using Dicalite BF filter aid. The filter cake containing nisin solids was recovered. Subsequently, the filter cake was dissolved in an aqueous HCl solution (pH 2.0 to 3.0). The mixture was stirred for at least one hour. The obtained solution containing nisin was filtered using dead-end filtration, depth filtration and sterile filtration at 10° C. to remove remaining solid components. The obtained liquid composition was kept at a pH of 2.0 to 3.0. The turbidity of the final product was 123 FNU, i.e. a turbid liquid composition was obtained. The obtained liquid nisin composition had a good antimicrobial activity, i.e. a MIC comparable to the MIC of composition C (see Example 2).

Example 9

Preparation of Stable Nisin Powder Suspension

Nisin powder (Silver Elephant, China) containing 2.5% w/w nisin and at least 50% w/w NaCl was suspended in water. Various thickening agents at various amounts were added. The pH was set at either pH 2 or pH 5 with HCl and NaOH solutions. The physical stability of the suspensions was analysed after storage for 9 days at room temperature by analyses of the height of the sedimentation front in a 50 ml tube containing 47.5 ml of the suspension. The results are depicted in the Table 5. The nisin concentration in all suspensions was 0.25% w/w. Sedimentation is expressed as the percentage clear liquid that was observed (i.e. the liquid that did not contain particles). 0% indicates that no sedimentation has occurred and that the suspension therefore has a good physically stability. The results show that at pH 2 and pH 5 the suspensions are physically stable when xanthan gum is used at a concentration higher than 0.05% (w/w). The results further show that at pH 2 and pH 5 the suspensions are physically stable when CMC or alginate are used at a concentration of 1% (w/w) or higher, while for HPMC a concentration of 3% (w/w) or higher leads to physical stable nisin suspensions.

TABLE 1

MIC values of nisin compositions in μg/ml against *M. luteus* and *P. aeruginosa*.

| Name | M. luteus | P. aeruginosa |
|---|---|---|
| Composition A | 0.015–0.0077 | >64800 |
| Composition B | 0.5–0.23 | >61200 |
| Composition C | 0.00012–0.00006 | 1900–1000 |
| Composition D | 0.012–0.006 | 6400–3200 |
| Composition E | 0.0004–0.0002 | >50000 |
| Composition F | 0.05–0.025 | >52000 |
| Composition G | 0.03–0.015 | >32000 |
| Composition H | 0.16–0.08 | >41000 |

TABLE 2

Days until respective micro-organism is reduced till below the detection limit of 1 CFU/ml in a beverage application with different nisin compositions.

| | Listeria monocytogenes | Leuconostoc oenos | Leuconostoc mesenteroides |
|---|---|---|---|
| Control | >4 | >4 | >4 |
| Composition A | 3 | 3 | 2 |
| Composition C | <1 | <1 | <1 |

TABLE 3

Amount of days that outgrowth of *Listeria monocytogenes* is inhibited below the detection limit of 10 CFU/ml in a food application model at 10° C. with different nisin compositions.

| | Amount of days that outgrowth is inhibited at 10° C. |
|---|---|
| Control | <1 |
| Composition A | 4 |
| Composition C | >25 |

TABLE 4

Amount of days that outgrowth of *Listeria monocytogenes* is inhibited below the detection limit of 10 CFU/ml in a food application model at room temperature with different nisin compositions.

| | Amount of days that outgrowth is inhibited at room temperature |
|---|---|
| Control | <1 |
| Composition A (250 μg/ml) | 2 |
| Composition A (500 μg/ml) | 3 |
| Composition C (250 μg/ml) | >25 |
| Composition C (500 μg/ml) | >25 |

TABLE 5

Physical stability of nisin powder suspension with different thickening agents.

| Thickening agent | Concentration thickening agent (% w/w) | Percentage sedimentation pH 2 (%) | Percentage sedimentation pH 5 (%) |
|---|---|---|---|
| No thickening agent | 0 | 79 | 77 |
| Xanthan gum | 0.05 | 79 | 79 |
| | 0.1 | 40 | 40 |
| | 0.2 | 0 | 0 |
| | 0.4 | 0 | 0 |
| | 1 | 0 | 0 |
| | 3 | 0 | 0 |
| | 5 | 0 | 0 |
| CMC | 0.05 | 92 | 93 |
| | 0.2 | 89 | 87 |
| | 0.4 | 87 | 79 |
| | 1 | 0 | 0 |
| | 3 | 0 | 0 |
| | 5 | 0 | 0 |
| HPMC | 0.05 | 81 | 94 |
| | 0.2 | 83 | 87 |
| | 0.4 | 83 | 87 |
| | 1 | 73 | 66 |
| | 3 | 40 | 11 |
| | 5 | 5 | 0 |
| Alginate | 0.05 | 72 | 94 |
| | 0.2 | 77 | 89 |
| | 0.4 | 63 | 58 |
| | 1 | 42 | 0 |
| | 3 | 0 | 0 |
| | 5 | 0 | 0 |

REFERENCES

Montville T J, Chung H J, Chikindas M L and Chen Y (1999), Nisin A depletes intracellular ATP and acts in bactericidal manner against *Mycobacterium smegmatis*. Letters in Appl. Microbiol. 28:189-193.

Mota-Meira M, LaPointe G, Lacroix C and Lavoie M C (2000), MICs of Mutacin B-NY266, Nisin A, Vancomycin, and Oxacillin against bacterial pathogens. Antimicrobial Agents and Chemotherapy 44:24-29.

Pongtharangkul T and Demirci A (2004). Evaluation of agar diffusion bioassay for nisin quantification, Appl. Microbiol. Biotechnol. 65:268-272.

The invention claimed is:

1. A method for preparing a liquid nisin composition, comprising the steps of:
    a) mixing powder nisin with an aqueous solution to prepare a first liquid nisin containing composition having a pH of 3.5 to 12 and a final inorganic salt concentration of 1.5 M or below,
    b) isolating solid compounds from the prepared first liquid nisin containing composition by centrifugation, filtration or any combination thereof,
    c) contacting the isolated solid compounds with a solution having a pH of 1 to 3 to prepare a second liquid nisin composition, and optionally
    d) removing solid compounds from the second liquid nisin composition.

2. The method according to claim 1, further comprising the step of: adjusting the pH of the second liquid nisin composition to a pH of 2 to 6.

3. A liquid nisin composition obtainable by the method according to claim 1.

4. The composition according to claim 3 having a minimum inhibitory concentration (MIC) of 0.001 μg/ml or less against *Micrococcus luteus* B212.

5. The composition according to claim 3, having a pH of 1.5 to 5.

6. The composition according to claim 3, wherein the composition comprises a salt to nisin ratio of 100:1 to 1:100.

7. The composition according to claim 3, having a turbidity of 0 to 100 FNU.

8. The composition according to claim 3, further comprising at least one compound selected from the group consisting of an additional antimicrobial compound, a surfactant, a pH adjusting agent, a cryoprotectant, an anti-foaming agent and a thickening agent.

9. A preservative for a food, feed or agricultural product comprising a composition according to claim 3.

10. A method for preserving a food, feed or agricultural product, wherein a composition according to claim 3, is applied to the food, feed or agricultural product.

11. A method for producing a solid nisin composition comprising the step of subjecting a composition according to claim 3, to a drying step, lyophilisation step, crystallisation step or precipitation step.

12. A food, feed or agricultural product comprising a composition according to claim 3.

13. The method according to claim 1, wherein the first liquid nisin containing composition of step a) has a pH of about 5.5 to about 7.5.

14. The method according to claim 1, wherein the first liquid nisin containing composition of step a) has a pH of about 5.5 to about 12.

* * * * *